(12) United States Patent
Peeters et al.

(10) Patent No.: US 10,358,521 B2
(45) Date of Patent: Jul. 23, 2019

(54) DURABLE HYDROGEN BONDED HYDROGELS

(71) Applicant: Suprapolix B.V., Eindhoven (NL)

(72) Inventors: Joris Wilhelmus Peeters, Horn (NL); Tristan Mes, Eindhoven (NL); Henricus Marie Janssen, Eindhoven (NL); Anton Willem Bosman, Eindhoven (NL)

(73) Assignee: SUPRAPOLIX B.V., Eindhoven (NL)

(*) Notice: Subject to any disclaimer, the term of this patent is extended or adjusted under 35 U.S.C. 154(b) by 140 days.

(21) Appl. No.: 15/329,534

(22) PCT Filed: Jul. 24, 2015

(86) PCT No.: PCT/NL2015/050545
§ 371 (c)(1),
(2) Date: Jan. 26, 2017

(87) PCT Pub. No.: WO2016/018145
PCT Pub. Date: Feb. 4, 2016

(65) Prior Publication Data
US 2017/0210843 A1 Jul. 27, 2017

(30) Foreign Application Priority Data
Jul. 28, 2014 (EP) .................................. 14178781

(51) Int. Cl.
| | | |
|---|---|---|
| A61K 9/00 | (2006.01) | |
| A61K 47/10 | (2017.01) | |
| A61L 24/00 | (2006.01) | |
| A61L 26/00 | (2006.01) | |
| C08G 65/333 | (2006.01) | |
| C08G 18/50 | (2006.01) | |
| C08G 65/329 | (2006.01) | |
| A61L 27/52 | (2006.01) | |
| A61K 8/87 | (2006.01) | |
| A61K 47/34 | (2017.01) | |
| A61Q 19/00 | (2006.01) | |
| C08G 18/75 | (2006.01) | |
| A61K 47/48 | (2006.01) | |

(52) U.S. Cl.
CPC ............. *C08G 18/506* (2013.01); *A61K 8/87* (2013.01); *A61K 9/0019* (2013.01); *A61K 47/10* (2013.01); *A61K 47/34* (2013.01); *A61L 24/0031* (2013.01); *A61L 26/008* (2013.01); *A61L 27/52* (2013.01); *A61Q 19/00* (2013.01); *C08G 18/755* (2013.01); *C08G 18/758* (2013.01); *C08G 65/329* (2013.01); *C08G 65/333* (2013.01); *C08G 65/33303* (2013.01); *C08G 65/33348* (2013.01); *C08G 65/33396* (2013.01); *A61K 9/0024* (2013.01); *A61K 2800/10* (2013.01); *C08G 2210/00* (2013.01); *C08G 2650/04* (2013.01); *C08G 2650/50* (2013.01); *C08L 2203/02* (2013.01)

(58) Field of Classification Search
CPC .................................................. C08G 65/329
USPC ........................................................ 528/7, 73
See application file for complete search history.

(56) References Cited

U.S. PATENT DOCUMENTS

| | | | |
|---|---|---|---|
| 5,410,016 | A | 4/1995 | Hubbell et al. |
| 6,320,018 | B1 | 11/2001 | Sijbesma et al. |
| 6,803,447 | B2 | 10/2004 | Janssen et al. |
| 7,622,131 | B2 | 11/2009 | Bosman et al. |
| 7,838,621 | B2 | 11/2010 | Janssen et al. |
| 8,246,990 | B2 | 8/2012 | Gemert et al. |
| 8,247,524 | B2 | 8/2012 | Janssen et al. |
| 8,268,952 | B2 | 9/2012 | Van Gemert et al. |
| 8,628,789 | B2 | 1/2014 | Baughman et al. |
| 8,673,286 | B2 | 3/2014 | Messersmith et al. |
| 8,754,213 | B2 | 6/2014 | Hoorne-van Gemert et al. |
| 8,883,188 | B2 | 11/2014 | Dankers et al. |
| 8,969,510 | B2 | 3/2015 | Bosman |
| 9,006,364 | B2 | 4/2015 | Van Gemert et al. |
| 9,006,386 | B2 | 4/2015 | Janssen et al. |
| 9,220,809 | B2 | 12/2015 | Brizard et al. |
| 9,339,586 | B2 | 5/2016 | Dankers et al. |
| 2014/0113989 | A1 | 4/2014 | Messersmith et al. |
| 2016/0115272 | A1 | 4/2016 | Mes et al. |

FOREIGN PATENT DOCUMENTS

| | | |
|---|---|---|
| WO | 9907343 A1 | 2/1999 |
| WO | 0144307 A2 | 6/2001 |
| WO | 2006118460 A1 | 11/2006 |
| WO | 2016018145 A1 | 2/2016 |

OTHER PUBLICATIONS

Dankers et al., Hierarchical Formation of Supramolecular Transient Networks in Water: A Modular Injectable Delivery System, Chem. Comm. 47, 7497, 2011.
Hirschberg et al., Helical Supramolecular Aggregates Based on Ureidopyrimidinone Quadruple Hydrogen Bonding, Chem. Eur. J. 9, 4222, 2003.
PCT International Search Report PCT/NL2015/050545 dated Sep. 10, 2015.
PCT International Search Report and Written Opinion PCT/NL2015/050545 dated Sep. 10, 2015.
Kieltyka et al., Mesoscale Modulation of Supramolecular Ureidopyrimidinone-Based Poly(ethylene glycol) Transient Networks in Water, J. Am. Chem. Soc.,135:11159, 2013.
Lee-Wang et al., Novel Supramoleculair Hydrogels as Artificial Vitreous Substitutes, Macromol. Symp. 296, 229, 2010.
Ramaekers et al., Self-Assembly of Chiral Supramolecular Ureido-Pyrimidinone-Based Poly(ethylene glycol) Polymers via Multiple Pathways, Macromolecules 47, 3823, 2014.

*Primary Examiner* — Duc Truong
(74) *Attorney, Agent, or Firm* — TraskBritt

(57) ABSTRACT

This disclosure relates to new injectable hydrogel materials that consist of water gellants comprising linear hydrophilic polymers that comprise hydrogen bonding units in the backbone combined with cross-linkable end groups, resulting in dynamic yet firm hydrogel materials that are easily processable, are highly elastic, show adhesive properties and are self-healing and are especially suitable for biomedical applications.

15 Claims, No Drawings

DURABLE HYDROGEN BONDED HYDROGELS

CROSS-REFERENCE TO RELATED APPLICATIONS

This application is a national phase entry under 35 U.S.C. § 371 of International Patent Application PCT/NL2015/050545, filed Jul. 24, 2015, designating the United States of America and published in English as International Patent Publication WO 2016/018145 A1 on Feb. 4, 2016, which claims the benefit under Article 8 of the Patent Cooperation Treaty to European Patent Application Serial No. 14178781.2, filed Jul. 28, 2014.

TECHNICAL FIELD

This application relates to injectable hydrogel materials that consist of water gellants comprising linear hydrophilic polymers that comprise hydrogen bonding units in the backbone combined with cross-linkable groups, resulting in dynamic yet firm hydrogel materials that are easily processable, highly elastic, self-healing, and that show adhesive properties.

BACKGROUND

Hydrogels can be characterized by three-dimensional networks of polymer chains that can be reversibly deformed. They absorb polar solvents such as water and they find applications in, for example, medical applications including bone transplants and tissue adhesives, drug delivery systems, pharmaceuticals and in water management.

Hydrogels can occur in the cross-linked form or in the uncross-linked form. Cross-linking usually provides stiffer gels due to strong increase of the molecular weight. Cross-linking can be achieved chemically by the formation of covalent bonds or physically by the formation of, e.g., hydrogen bonds or ionic interactions. Obviously, cross-linking can also be achieved by both chemical and physical means.

Chemical cross-linking of hydrophilic polymers is a general and often applied route to obtain hydrogels. In order to be able to administer or process these gels, prepolymers are dissolved in water and are then polymerized resulting in (in situ) hydrogel formation. Hydrogellation procedures are often based on the use of acrylic or methacrylic macromonomers that are not preferred in (biomedical) applications, because of their inherent toxicity and because they usually require a potentially hazardous initiator for polymerization. Moreover, cross-linked hydrogels lack reversibility and are limited in their degradation behavior, as poly(acrylates) and poly(methacrylates) are not biodegradable.

For example, U.S. Pat. No. 5,410,016, incorporated by reference, discloses hydrogels based on copolymers of poly(ethylene glycol) with poly(DL-lactide) containing pendant acrylate functions that are cross-linked in situ.

WO 01/44307, incorporated by reference, discloses hydrogels based on polyvinyl alcohol modified with pendant acrylate and methacrylate groups that are chemically cross-linked in situ. Hence, in both patent documents, an irreversible cross-linked hydrogel is obtained by starting from water-processable prepolymers that contain reactive groups. Because a relative high level of cross-links is needed to gel these materials, the resulting hydrogels are rigid and lack beneficial elastic behavior.

U.S. Pat. No. 8,673,286, incorporated by reference, discloses branched 4-arm poly(ethyleneglycol) materials end-functionalized with DOPA-groups (3,4-dihydroxyphenyl alanine), which aqueous formulations upon oxidative cross-linking result in adhesive hydrogels with 15-30 wt % solids content.

U.S. Patent Publication 2014/0113989, incorporated by reference, discloses branched 4-arm poly(ethyleneoxide)-poly(propylene oxide) copolymers materials end-functionalized with DOPA-groups that display negative swelling hydrogels upon oxidative cross-linking.

Messersmith et al., *Chem. Comm.* 47:7497, 2011, incorporated by reference, discloses a pH-responsive hydrogel resulting from a cross-linked polymer made by reacting a branched 4-arm poly(ethyleneglycol) materials end-functionalized with DOPA-groups with bifunctional boronic acid moieties. Clearly, this approach needs two different ingredients in a specific ratio to obtain a gel. Moreover, this system is only gelled at an alkaline pH of 9 and boronic acid derivatives are needed, which makes the biomedical application of this hydrogel system difficult due to the high pH and the increased concerns about the detrimental health effects of boric acid derivatives. The resulting hydrogels are tacky and, therefore, obviously demonstrate self-adhesive behavior.

WO 99/07343, incorporated by reference, discloses thermally reversible hydrogels intended for uses in drug delivery applications that are based on a hydrophilic polyethylene glycol block and hydrophobic PLLA (poly-L-lactic acid) blocks. The gelling is governed by the presence of the crystalline hard blocks formed by the PLLA. The presence of the crystalline PLLA-blocks limits the mechanical properties and the biodegradation of these materials to a great extent.

In general, "supramolecular chemistry" is understood to be the chemistry of physical or non-covalent, oriented, multiple (at least two), co-operative interactions. For instance, a "supramolecular polymer" is an organic compound that has polymeric properties, for example, with respect to its rheological behavior due to specific and strong secondary interactions between the different molecules. These physical or non-covalent supramolecular interactions contribute substantially to the properties of the resulting material.

Supramolecular polymers comprised of (macro)molecules that bear hydrogen bonding units can have polymer properties in bulk and in solution because of the hydrogen bridges between the molecules. Sijbesma et al. (U.S. Pat. No. 6,320,018 and *Science* 278:1601, 1997, both incorporated by reference) have shown that in cases where a self-complementary quadruple hydrogen bonding unit (4H-unit) is used, the physical interactions between the molecules become so strong that polymers with much improved material properties can be prepared.

WO 2006/118460, incorporated by reference, discloses supramolecular hydrogel materials comprising water gellants that are comprised of hydrophilic polymers to which at least two 4H-units are covalently attached via urethane-alkyl moieties. However, it appeared that these hydrogel materials are insufficient in strength for several applications and their viscosity is too high at biomedically relevant temperatures to allow administration via liquid processing techniques like injection through a syringe.

EP 1.972.661 A1, incorporated by reference, discloses supramolecular hydrogels that comprise 4H-units, together with urea bonding-motifs in a hydrophilic polymer. These hydrogels are thermo-reversible due to their supramolecular nature. However, their reversible nature may also result in dissolving of the gel when an excess amount of water is present such as inside the body.

Dankers et al., *Adv. Healthcare Mat.* 3:87, 2014, incorporated by reference, discloses that a hydrogel of a specific embodiment of EP 1.972.661 A1, consisting of a poly (ethyleneglycol) of 10,000 Da with 4H-unit end groups, can be rendered injectable only when dissolved in strongly basic aqueous solution with a pH higher than 8.5, which is not favored for biomedical applications. Moreover, the resulting hydrogel has very limited elastic strength.

Dankers et al., *Adv. Mater.* 24:2703, 2012, incorporated by reference, discloses transient networks based on bifunctional supramolecular polymers consisting of polyethylene glycol which is end-functionalized with 4H-units. The 4H-units are shielded by hydrophobic alkylene groups comprising a urea moiety for lateral hydrogen bonding. The transient networks are only formed by supramolecular interactions between the polymer chains.

Hirschberg et al., *Chem. Eur. J.* 9:4222, 2003, incorporated by reference, discloses mono- and bifunctional compounds comprising one or two 4H-units, respectively. Some of the bifunctional compounds have been shown to form polymers in apolar solvents by intermolecular supramolecular interactions only.

Kieltyka et al., *J. Am. Chem. Soc.* 135:11159, 2013, incorporated by reference, discloses the bifunctional supramolecular polymers as Dankers et al., *Adv. Mater.* 24:2703, 2012, as well as the corresponding monofunctional supramolecular polymers. Transient networks based on mixtures of the bifunctional and monofunctional supramolecular polymers are only formed by supramolecular interactions between the polymer chains.

Ramaekers et al., *Macromolecules* 47:3823, 2014, incorporated by reference, discloses chiral derivatives of the bifunctional supramolecular polymers as Dankers et al., *Adv. Mater.* 24:2703, 2012. In water, these polymers may form helical fibers by supramolecular interactions between the polymer chains.

Lee-Wang et al., *Macromol. Symp.* 296:229, 2010, incorporated by reference, discloses telechelic PPG-PEG-PPG polymers, which end-functionalized with 4H-units. These polymers are reported to have a low solubility in water and do not form hydrogels, although associating behavior of the 4H-units was observed.

Because of the shortcomings of state-of-the-art hydrogels, there is a need for synthetic polymers that are injectable, can gel water upon command, need only a limited amount of cross-links to gel, are highly elastic, are able to dissipate energy, and display self-healing behavior. In addition, it is desired that hydrogels can be tuned with respect to their mechanical properties to be able to meet the requirements of specific applications. Also, it would be advantageous to be able to make biodegradable reversible hydrogels.

BRIEF SUMMARY

Provided are injectable hydrogels using a polymeric gellant that comprises both strong and reversible hydrogen bonding units and durable chemical cross-linkable groups. Further provided is a process to prepare such new hydrogels. With this disclosure, easy administration of hydrogels is combined with high strength and elasticity, without the need for high cross-linking densities due to the additional presence of the reversible hydrogen bonding motifs. Moreover, the hydrogels according to the disclosure are tunable in their mechanical properties, and offer tissue-adhesion, durability, and self-healing properties, while it is optional to make the hydrogels biodegradable.

This disclosure, therefore, relates to a water gellant comprising a hydrophilic polymer backbone P, a cross-linkable group D, a hydrogen bonding 4H-unit 4H, having the structure according to formula (A) or formula (B) or formula (C):

  (A)

or

  (B)

or

  (C)

wherein:
n is in the range of 1 to 10;
a is 0 or 1;
b is 0 or 1;
q is in the range of 1 to 10;
4H represents the 4H-unit that has the general formula (1') or (2'):

  (1')

  (2')

In the general formulas shown above, the C—$X_i$ and C—$Y_i$ linkages each represent a single or double bond, n is 4 or more and $X_1 \ldots X_n$ represent donors or acceptors that form hydrogen bridges with the H-bridge-forming unit containing a corresponding structural element (2) linked to them, with $X_i$ representing a donor and $Y_i$ an acceptor or vice versa. Properties of the 4H-unit having general formulas (1') and (2') are disclosed in U.S. Pat. No. 6,320,018, which is expressly incorporated herein by reference.

This disclosure also relates to a process for preparing a water gellant comprising a hydrophilic polymer backbone P, a cross-linkable group D, and a 4H-unit 4H, having the structure according to formula (A) or formula (B) or formula (C), the process comprising reacting a polymer component P—$(F)_v$, a 4H-unit 4H—(F), and a cross-linking component $(F)_x$-L-Z, wherein:
F represents a reactive end group selected from the group consisting of hydroxy, amine, thiol, isocyanate, carboxylic acid, carboxylic ester, and combinations of these end groups;
v is in the range of 1-4;
w is in the range of 1-4;
x is in the range of 1-4;
L represents a linker moiety, and
Z represents a group that can cross-link.

This disclosure also relates to a process for preparing a water gellant comprising a hydrophilic polymer backbone P, a cross-linkable group D, and a 4H-unit 4H, having the structure according to formula (A) or formula (B) or formula (C), the process comprising reacting a polymer component P—$(F)_v$, a precursor of the 4H-unit according to the formula 4H*—$(F)_w$ and a cross-linking component $(F)_x$-L-Z, wherein:
- F represents a reactive end group selected from the group consisting of hydroxy, amine, thiol, isocyanate, carboxylic acid, carboxylic ester, and combinations of these end groups;
- v is in the range of 1-4;
- w is in the range of 1-4;
- x is in the range of 1-4;
- L represents a linker moiety; and
- Z represents a group that can cross-link.

It further relates to a liquid aqueous formulation comprising:
- (a) 0.3-80.0 wt. %, based on the total weight of the formulation, of a water gellant; and
- (b) 20.0 to 99.7 wt. % water;

wherein the aqueous formulation is injectable and can be transformed into an elastic hydrogel upon cross-linking of the D moieties.

This disclosure also relates to a process for preparing a hydrogel, wherein a liquid aqueous formulation comprising:
- (a) 0.3-80.0 wt. %, based on the total weight of the formulation, of a water gellant; and
- (b) 20.0 to 99.7 wt. % water;

is reacted with an auxiliary A that initiates or mediates the cross-linking reaction of the D moieties in the water gellant.

DETAILED DESCRIPTION

The verb "to comprise" and its conjugations as used in this description and in the claims are used in their non-limiting sense to mean that items following the word are included, but items not specifically mentioned are not excluded.

In addition, reference to an element by the indefinite article "a" or "an" does not exclude the possibility that more than one of the element is present, unless the context clearly requires that there is one and only one of the elements. The indefinite article "a" or "an" thus usually means "at least one."

When investigating supramolecular hydrophilic polymers comprising quadruple hydrogen bonding units (4H-units), it was found that by introduction of chemical cross-linkable groups in the polymers, a new class of supramolecular hydrogel materials was obtained. Due to the synthetic and functional orthogonality of the reversible hydrogen bonding and the covalent cross-links, new hydrogel materials were obtained that combine the robustness of permanently cross-linked high molecular weight hydrogels with the dynamic nature of the reversible low molecular weight supramolecular hydrogels, resulting in hydrogels with advantageous properties like very high strength, elasticity, biodegradability, stress-relaxation, self-healing properties, and injectability. Moreover, the reversibility of the supramolecular hydrogen bonding interaction allows for temperature and pH-dependent performance and the possibility to easily fine-tune material properties by supramolecular blending of other materials comprising the same hydrogen bonding unit. Additionally, the reversible supramolecular interaction can also favor the biodegradation of the hydrogel material.

In this document, the structure of the water gellant according to this disclosure and its preparation are disclosed, as well as the components of the gellant: (i) the hydrogen bonding 4H-unit, (ii) the polymer backbone P and (iii) the cross-linkable group D. Finally, the liquid aqueous formulations and the hydrogels that can be prepared from the water gellants are disclosed.

General Definitions

In this document, the terms "moiety" and "group" are used interchangeably.

A urea moiety as indicated in this document is to be understood as a moiety according to the formula:

$$—NR^a—C(X)—NR^a—$$

wherein X is O or S, preferably O, $R^a$ is, independently, a hydrogen atom or a linear, branched or cyclic $C_1$-$C_{12}$ alkyl group, preferably a hydrogen atom. $R^a$ is more preferably a hydrogen atom or a linear, branched or cyclic $C_1$-$C_6$ alkyl group, most preferably a hydrogen atom.

An amide moiety as indicated in this document is to be understood as a moiety according to the formula:

$$—NR^a—C(X)—$$

wherein X and $R^a$ are as described above.

A urethane moiety as indicated in this document is to be understood as a moiety according to the formula:

$$—NR^a—C(X)—X—$$

wherein X and $R^a$ are as described above (X can independently be O or S).

An ester moiety as indicated in this document is to be understood as a moiety according to the formula:

$$—C(X)—X—$$

wherein X is as described above (X can independently be O or S).

A carbonate moiety as indicated in this document is to be understood as a moiety according to the formula:

$$—X—C(X)—X—$$

wherein X is as described above (X can independently be O or S).

An amine moiety as indicated in this document is to be understood as a moiety according to the formula:

$$—N(R^a)—$$

wherein $R^a$ is as described above.

An ether moiety as indicated in this document is to be understood as a moiety according to the formula:

$$—X—$$

wherein X is as described above.

An isocyanate group is to be understood as a —NCX group, wherein X is as described above.

A hydroxy group is to be understood as a —OH group.

An amine group is to be understood as a —$N(R^a)_2$ group, wherein $R^a$ is as described above.

A thiol group is to be understood as a —SH group.

A carboxylic acid group is to be understood as a group according to the formula:

$$—C(X)—XH$$

wherein X is as described above (X can independently be O or S).

A carboxylic ester group is to be understood as a group according to the formula:

$$—C(X)—XR^a$$

wherein X is as described above (X can independently be O or S) and wherein $R^a$ is not hydrogen.

Acrylate and methacrylate groups are to be understood as $R^b$—C(=CH$_2$)—C(X)—X— groups, wherein X is as described above (X can independently be O or S), and wherein $R^b$ is hydrogen or methyl. It is, however, preferred that in acrylate and methacrylate groups, X is O.

Acrylamide and methacrylamide groups are $R^b$—C(=CH$_2$)—C(X)—N($R^a$)— groups, wherein X and $R^a$ are as described above, and wherein $R^b$ is hydrogen or methyl. It is, however, preferred that in acrylamide and methacrylamide groups, X is O.

The Structure of the Water Gellant and its Preparation

The water gellant of this disclosure has the general structure:

    (A)

or

    (B)

or

    (C)

wherein P, 4H and D are as defined above.

The water gellant according to formula (A), formula (B) or formula (C) may have terminal end groups that originate from the reactants, as will be apparent to the person skilled in the art.

The water gellant has a molecular weight of about 800 to about 1,000,000, preferably about 1,000 to about 60,000, more preferably about 1,000 to about 20,000, and most preferably about 2,000 to about 10,000 Dalton.

The 4H-units can be attached to the polymer backbone P in any way, e.g., by grafting onto the polymer backbone, by attachment to multiple, i.e., two or more, end groups of the polymer backbone, or the 4H-units can be an integral part of the backbone of the polymer that constitutes the water gellant. As will be understood by the person skilled in the art, the 4H-units may also be attached by a combination of these bonding modes.

It is preferred that the polymer backbone P is connected to a 4H-unit via a direct bond, (thio)urea, (thio)urethane, amide, ester, carbonate, secondary amine, tertiary amine and/or ether moiety. It is, however, more preferred that the polymer backbone P and the 4H-unit are connected via a direct bond, (thio)urea, (thio)urethane, carbonate, and/or an amide moiety; even more preferably, via a direct bond, urea, and/or urethane moiety; most preferably, via a direct bond and/or urethane moiety.

The cross-linkable groups D can be attached to the polymer backbone P in any way, e.g., by grafting onto the polymer backbone, by attachment to multiple, i.e., two or more, end groups of the polymer backbone, or the cross-linkable group D can be an integral part of the backbone of the polymer that constitutes the water gellant. As will be understood by the person skilled in the art, the cross-linkable groups D may also be attached by a combination of these bonding modes.

It is preferred that the polymer backbone P is connected to the cross-linkable groups D via a (thio)urea, (thio)urethane, amide, ester, carbonate, secondary amine, tertiary amine and/or ether moiety. It is, however, more preferred that the polymer backbone P and the cross-linkable group D are connected via a (thio)urea, (thio)urethane, ester, and/or an amide moiety, even more preferably, via a urea and/or urethane moiety, and most preferably, via a urea moiety.

In a preferred embodiment of this disclosure, the 4H-units form an integral part of the backbone of the polymer and the water gellant has a linear structure according to Formula (A) or (B) or (C). More preferably, the cross-linkable groups D are present as end groups in the polymer and the water gellant has the structure according to Formula (A).

The polymer backbone P can be multifunctional but is preferably bifunctional, meaning that it has about 1.8 to about 2 end groups, preferably about 1.9 to about 2 end groups, and most preferably higher than about 1.95 to about 2 end groups The number of repeating units n is at least 1 and not higher than 10, more preferably not higher than 6, and most preferably not higher than 3.

The number of repeating units q is at least 1 and not higher than 10, more preferably at least 2, even more preferably at least 3, and most preferably at least 5.

The number of repeating units a is 0 or 1; more preferably 1.

The number of repeating units b is 0 or 1; more preferably 0.

The water gellant can be prepared by three methods: (i) P, D, and the 4H-unit are all mixed together in one step and covalently attached to each other; (ii) P is first covalently attached to the 4H-unit, followed by covalently end-capping or chain extension with D; or (iii) P is first covalently attached to D followed by covalent chain extension with the 4H-unit.

Preferably, method (ii) is used to produce the water gellant.

The 4H-unit may be used as such or may be formed (optionally in situ in one of the methods (i), (ii) or (iii)) from a precursor of the 4H-unit (in this document, indicated as a 4H*-unit) of the formula 4H*—(F)$_w$ and a reactive end group F from one of the other reaction partners P and/or D or a reactive end group from a further reagent E-F$_y$ wherein y is 1 or 2, as is described in the section "The 4H-Unit." For example, the 4H*-unit 2-amino-4-hydroxy-5-(2-hydroxyethyl)-6-methyl-pyrimidine (w is 2) may be reacted with two molar equivalents of isophorone diisocyanate to form the corresponding 4H-unit:

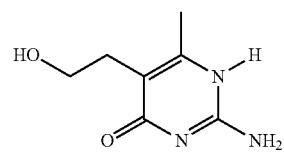

-continued

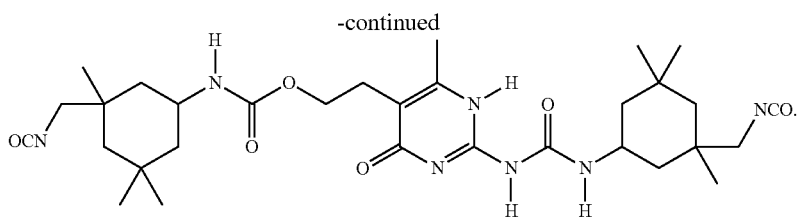

10

Alternatively, the 4H*-unit 2-amino-4-hydroxy-5-(2-hydroxy ethyl)-6-methyl-pyrimidine (w is 2) may, for example, react with a polymer P having suitable reactive end groups (e.g., isocyanate end groups) to form the corresponding 4H-unit. Reference is made to the section "The Polymer Backbone P."

Preferably, E is a cyclic, linear or branched $C_1$-$C_{24}$ alkyl or alkylene group, a $C_6$-$C_{24}$ aryl or arylene group, a $C_7$-$C_{24}$ alkaryl or alkarylene group, or a $C_7$-$C_2$4 arylalkyl or arylalkylene group, wherein these groups optionally, but not preferably, comprise 1-5 heteroatoms selected from the group consisting of O, N and S.

Accordingly, the process for preparing the water gellant comprises reacting a polymer component P—$(F)_v$, a 4H-unit 4H—$(F)_w$, and a cross-linking component $(F)_x$-L-Z, wherein:
F represents a reactive end group selected from the group consisting of hydroxy, amine, thiol, isocyanate, carboxylic acid, carboxylic ester, and combinations of these end groups;
v is in the range of 1-4,
w is in the range of 1-4;
x is in the range of 1-4;
L represents a linker moiety, and
Z represents a group that can cross-link.

This disclosure also relates to a process for preparing a water gellant comprising a hydrophilic polymer backbone P, a cross-linkable group D, and a 4H-unit 4H, having the structure according to formula (A) or formula (B) or formula (C), the process comprising reacting a polymer component P—(F), a precursor of the 4H-unit according to the formula 4H*—$(F)_w$, and a cross-linking component $(F)_x$-L-Z, wherein:
F represents a reactive end group selected from the group consisting of hydroxy, amine, thiol, isocyanate, carboxylic acid, carboxylic ester, and combinations of these end groups;
v is in the range of 1-4;
w is in the range of 1-4;
x is in the range of 1-4;
L represents a linker moiety; and
Z represents a group that can cross-link.
Preferably, v is in range of 1-2.
Preferably, w is in range of 1-2.
Preferably, x is in range of 1-2.

In these processes, it is preferred that P, D, and the 4H-unit are covalently connected to each other by moieties selected from the group consisting of (thio)urea, (thio)urethane, amide, ester, carbonate, secondary amine, tertiary amine and ether moieties and combinations thereof. As will be apparent to the skilled person, the polymer backbone P, the cross-linkable group D and the 4H-unit are furnished with functional groups that are capable of providing the connecting moieties described above.

The methods (i), (ii), and (iii) can be executed in the bulk or in solution. Reaction solvents are preferably aprotic solvents known in the art, such as ethers, such as diethyl ether, THF, methyl-tetrahydrofuran, dioxane and methyl-tert-butyl ether, DMSO, dimethyl acetamide, DMF, NMP, chloroform, dichloromethane, diethylcarbonate, propylene carbonate, ketones such as acetone, MEK and methyl-tert-butyl ketone, esters such as ethyl acetate and butyl acetate, and toluene.

Preferably, the reactants and solvents are dried, i.e., containing little or no water. Preferably, the reaction is executed under an inert atmosphere of nitrogen or argon.

The water gellant can be isolated by different types of work-up procedures that are known in the art, such as precipitation, extraction, washing, drying, filtration and evaporation procedures, or combinations thereof.

Preferably, the reaction is performed with less than about 25% by weight of solvent, more preferably less than about 15% by weight of solvent, and most preferably without solvent, at temperatures in between about 100° C. and 150° C., possibly by using a twin-screw extruder, kneader or mixer.

The 4H-Unit

It is preferred that the 4H-unit is an essentially planar or flat structure.

If the 4H-unit is capable of forming four hydrogen bridges, which is preferred according to the disclosure, the 4H-unit has preferably the general formula (1) or (2):

Properties of the 4H-unit having general formulas (1) and (2) are disclosed in U.S. Pat. No. 6,320,018, which is expressly incorporated herein by reference.

It is, therefore, preferred that in formulas (1) and (2), n equals 4 so that the 4H-unit comprises four donors or acceptors $X_1 \ldots X_4$ and $Y_1 \ldots Y_4$. The 4H-unit may be self-complementary (i.e., the two hydrogen-bonded units $X_1 \ldots X_4$ and $Y_1 \ldots Y_4$ have an equal array of donors and acceptors) or non self-complementary (i.e., the two hydrogen-bonded units $X_1 \ldots X_4$ and $Y_1 \ldots Y_4$ have two different arrays of donors and acceptors). Preferably, the 4H-unit comprises two successive donors, followed by two successive acceptors, i.e., that it is preferred that $X_1$ and $X_2$ are donors and $X_3$ and $X_4$ are acceptors. Preferably, the donors and acceptors are O, S, and N atoms. This 4H-unit is in detail disclosed in U.S. Pat. No. 6,320,018, which is specifically incorporated by reference herein.

According to a preferred embodiment of this disclosure, the 4H-unit has the general formula (3) or formula (4) and tautomers thereof:

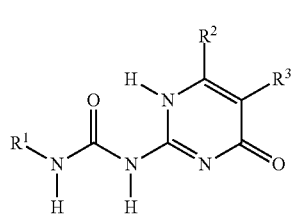
(3)

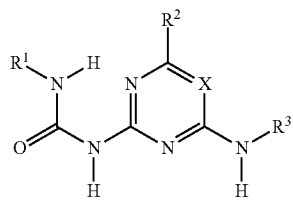
(4)

wherein X is a nitrogen atom or a carbon atom bearing a substituent $R^8$, preferably X is a nitrogen, and wherein $R^1$, $R^2$, $R^3$ and $R^8$ are selected from the group consisting of:
(a) hydrogen;
(b) $C_1$-$C_{20}$ alkyl;
(c) $C_6$-$C_{12}$ aryl;
(d) $C_7$-$C_{12}$ alkaryl;
(e) $C_7$-$C_{12}$ alkylaryl;
(f) polyester groups having the formula (5),

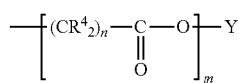
(5)

wherein $R^4$ and Y are independently selected from the group consisting of hydrogen and $C_1$-$C_6$ linear or branched alkyl, n is 1-6 and m is 10 to 100;
(g) $C_1$-$C_{10}$ alkyl groups substituted with 1-4 ureido groups according to the formula (6), $R^5$—NH—C(O)—NH— (6)

wherein $R^5$ is selected from the group consisting of hydrogen and $C_1$-$C_6$ linear or branched alkyl;
(h) polyether groups having the formula (7),

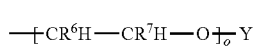
(7)

wherein Y, $R^6$ and $R^7$ are independently selected from the group consisting of hydrogen and $C_1$-$C_6$ linear or branched alkyl and o is 10-100, and wherein the 4H-unit is bonded to the polymer backbone P via $R^1$, $R^2$ and/or $R^3$ (so that $R^1$, $R^2$ or $R^3$ represent a direct bond) with the other R groups independently representing a side chain according to (a)-(h).

As will be apparent to the person skilled in the art, the groups (b)-(h) defined above may be linear, branched or cyclic where appropriate.

In a first preferred embodiment, the 4H-unit is bonded to a polymer backbone P via $R_1$ and $R_2$ (so that $R_1$ and $R_2$ constitute direct bonds), while $R_3$ is any one of the groups (a)-(h) defined above, preferably group (a) or (b), more preferably group (a).

In a second preferred embodiment, the 4H-unit is bonded to a polymer backbone P via $R_1$ and $R_3$ (so that $R_1$ and $R_3$ constitute a direct bond), while $R_2$ is any one of the groups (a)-(h) defined above, preferably group (b), more preferably isopropyl or methyl and most preferably methyl. Most preferably for this second preferred embodiment, the 4H-unit is bonded to a polymer backbone P via $R_1$ and $R_3$, while $R_2$ is any one of the groups (a)-(h) defined above, preferably group (b), more preferably isopropyl or methyl and most preferably methyl.

The 4H-unit building blocks that are used to prepare the water gellants of this disclosure are furnished with functional groups that are part of the $R_1$, $R_2$ and $R_3$. The functional groups are preferably (thio)isocyanates, (activated) amines, alcohols, thiols, (activated) esters, acrylates, methacrylates, acryl amides, methacryl amides or other vinyl groups, more preferably isocyanates, (activated) amines, or alcohols, even more preferably isocyanates or (activated) amines, most preferably isocyanates.

Precursors of the 4H-unit (4H*) are nitrogen-containing compounds that are reacted with isocyanates or activated amines, or that are activated and reacted with primary amines, to obtain a urea moiety that is part of the quadruple hydrogen bonding site. The nitrogen-containing compound is preferably an isocytosine derivative (i.e., a 2-amino-4-hydroxy-pyrimidine derivative) or a triazine derivative, or a tautomer and/or enantiomer of these derivatives. More preferably, the nitrogen-containing compound is an isocytosine derivative having an aliphatic-substituent containing a functional group in the 5-position and an alkyl-substituent in the 6-position, most preferably, 2-hydroxy-ethyl or propionic acid ester in the 5-position and methyl in the 6-position, most preferably, the precursor of the 4H-unit is 5-(2-hydroxy ethyl)-6-methyl isocytosine.

In a preferred embodiment, the precursor of the 4H-unit according to the formula 4H*—(F), is represented by formula (11) or formula (12):

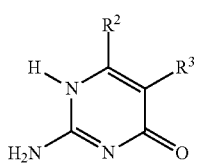
(11)

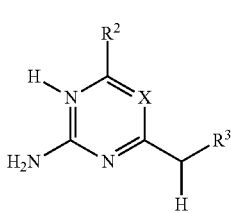

(12)

wherein $R^2$, $R^3$ and X have the meaning as defined for formulas (3) and (4).

In another preferred embodiment of this disclosure, the 4H-unit is a simple hydrogen-bonding unit (SHB-unit) selected from the group consisting of a (thio)urea, a bisureido, an amide, a bisamide or a (thio)urethane moiety. More preferably, it is a bisureido or bisamide moiety and has the general formula (8), (9), or (10):

—NH—C(O)—NH—K—NH—C(O)—NH—     (8)

—NH—C(O)—K—C(O)—NH—     (9)

—C(O)—NH—K—NH—C(O)—     (10)

in which K is selected from the group consisting of a direct covalent bond, cyclic, linear or branched $C_1$-$C_{24}$ alkylene groups, $C_6$-$C_{24}$ arylene groups, $C_7$-$C_{24}$ alkarylene groups and $C_7$-$C_{24}$ arylalkylene groups, wherein the alkylene groups, arylene groups, alkarylene groups and arylalkylene groups optionally, but not preferably, comprise 1-5 heteroatoms selected from the group consisting of O, N and S, more preferably K is selected from a direct bond, cyclic or linear $C_1$-$C_{24}$ alkylene groups, and $C_6$-$C_{24}$ arylalkylene groups, most preferably K is selected from linear $C_2$-$C_{12}$ alkylene groups.

Water gellants comprising an SHB-unit can be characterized by formula (D), formula (E) and/or formula (F):

D-[(SHB)]$_b$—[P—(SHB)]$_n$—[P]$_a$-D     (D)

or

{—(SHB)$_b$—[P—(SHB)]$_n$—[P]$_a$-D-}$_q$     (E)

or

{—[SHB]$_n$—[P-D]$_q$-}     (F)

The water gellant according to formula (D) or formula (E) or formula (F) may have terminal end groups that originate from the reactants as will be apparent to the person skilled in the art.

In another preferred embodiment, the SHB-unit is preferably formula (8) and the nitrogen-containing compound that is the precursor of this 4H-unit (i.e., the SHB component; see below) is preferably selected from hydrazine, 1,2-diaminoethane, 1,3-diaminopropane, 1,4-diaminobutane, 1,5-diaminopentane, 1,6-diaminohexane, 1,4-diaminocyclohexane, 1,7-diaminoheptane, 1,8-diaminooctane, 1,6-diamino 3,3,4-trimethylhexane, 1,10-diaminodecane, 1,11-diaminoundecane, 1,12-diaminododecane, methylene dicyclohexane 4,4-diamine, 1,3-bis(aminomethyl)benzene, 1,4-bis(aminomethyl)benzene, and methylene diphenyl diamine, more preferably hydrazine, 1,2-diaminoethane, 1,4-diaminobutane, 1,6-diaminohexane, trans-1,4-diaminocyclohexane, 1,10-diaminodecane, and 1,12-diaminododecane, most preferably 1,4-diaminobutane and 1,6-diaminohexane.

A process for preparing the water gellant based on general formulas (8), (9) and (10) comprises reacting a polymer component P—(F)$_v$, an SHB component and a cross-linking component (F)$_x$-L-Z, wherein P, F, L, Z, v, w and x are defined as above. The SHB component is selected from the group consisting of mono- and difunctional compounds comprising 0 to 20 carbon atoms, preferably 4 to 13 carbon atoms. The mono- and difunctional compounds are selected from the group consisting of (di)isocyanates, (di)thioisocyanates, (di) amines that are optionally activated, (di)acid chlorides, (di)esters that are optionally activated, (di)ols that are optionally activated, (di)acryl amides, (di)methacryl amides or (di)thiols that are optionally activated. Preferably, the mono- and difunctional compounds are selected from the group consisting of (di)isocyanates, (di) activated amines or (di) activated esters. Most preferably, the mono- and difunctional compounds are (di)amines. Suitable examples are hexylamine, dodecylamine, 1,6-hexyldiamine, 1,10-decyldiamine, isophorone diamine, adipoyl chloride, glutaryl chloride, succinyl chloride, undecenoyl chloride.

The water gellant based on general formulas (8), (9) and (10) can be prepared by the three methods: (i), (ii) and (iii) described above but is preferably prepared with method (ii). Hence, a polymer component P—(F)$_v$ is reacted with the mono- or difunctional compound described above, followed by covalently end-capping or chain extension with (F)$_x$-L-Z.

The Polymer Backbone P

The polymer backbone P has a molecular weight of about 250 to about 50,000, preferably about 3,000 to about 30,000, more preferably about 5,000 to about 15,000, more preferably about 5,000 to about 10,000, and most preferably about 5,000 to about 8,000 Dalton.

The polymer backbone P is preferably a hydrophilic polymer, and according to this disclosure, a hydrophilic polymer is defined as a polymer having a solubility in water of at least about 1 g/L.

P may represent any type of polymer backbone known in the art, such as polyethers, polyesters, polycarbonates, polyamides, polyoxazolines, polyacrylates, polymethacrylates, polyolefins, hydrogenated polyolefins, polysiloxanes, polycarbonates, (per)fluorinated polyethers, polyvinylenes, or co-polymers of such polymers. More preferably, the polymer backbone is a polyether, polyester, polycarbonate, polyamide, polyoxazoline, polyacrylate, polymethacrylate, polyolefin, hydrogenated polyolefin, polycarbonate, polyvinylene, or a co-polymer of such polymers. Even more preferred are polyethers, polyesters, polycarbonates, or copolymers thereof. Most preferably, P is a polyether, preferably a polyglycol, preferably a polyethylene glycol or a polyethylene-co-propylene glycol (random or block), and most preferably a polyethylene glycol.

Although some of the above-listed polymer backbones P themselves may not be hydrophilic per se, co-polymerizing them with the right amount of water-soluble polymer, or use of a combination of these polymer backbones P can lead to a water gellant, as will be obvious to a person skilled in the art.

The polymer backbone P that is used to prepare the water gellant of this disclosure can have different numbers of functional groups. The average functionality of the functional polymer is preferably about 1.5 to about 2, more preferably about 1.8 to about 2, and most preferably about 1.9 to about 2.

The polymers P that are used to prepare the water gellant of this disclosure can have different functional groups, such as, for example, alcohols, amines, thiols, isocyanates, carboxylic acids or combinations of these end groups. Preferably, the functional groups are alcohols or isocyanates, most preferably isocyanates. In this most preferred embodiment, the polymer backbone P is derived from a polymer having two hydroxy end groups after reaction with about 2 to 6 molar equivalents of diisocyanate, preferably with about 2 to 3, and most preferably with about 2 molar equivalents of diisocyanate to form an isocyanate functional polymer. The diisocyanates are preferably selected from the group consisting of 1,ω-diisocyanates comprising 1 to 20 carbon atoms, more preferably from the group consisting of toluene diisocyanate (TDI), methylene diphenyl diisocyanate (MDI), methylene dicyclohexane 4,4-diisocyanate (HMDI), isophorone diisocyanate (IPDI), hexane diisocyanate (HDI), 1,6-diisocyanato-2,2,4-trimethylhexane, 1,6-diisocyanato-2,4,4-trimethylhexane, 1,3-xylylene diisocyanate, 1,4-xylylene diisocyanate and uretdione dimers of HDI, more preferably from the group consisting of IPDI, HMDI, HDI, 1,6-diisocyanato-2,2,4-trimethylhexane and 1,6-diisocyanato-2,4,4-trimethylhexane. Most preferably, the diisocyanate is isophorone diisocyanate (IPDI) or methylene dicyclohexane 4,4-diisocyanate (HMDI).

The polymer backbones P that are used to prepare the water gellant of this disclosure can be combinations of polymers with different backbone compositions, different architectures, different molecular weights and/or a different (numbers of) functional groups. For example, one can use a telechelic polyethylene glycol with a molecular weight of about 5000 Dalton in combination with a telechelic polyester with a molecular weight of about 500 Dalton.

Examples of telechelic polymers with hydroxyl end groups that can be used for polymer backbone P are (a) polyetherdiols having a polyoxyalkylene structure, such as polyethylene glycols, polypropylene glycols, poly(ethylene-co-propylene) glycols (random or block), poly(ethylene-block-propylene-block-ethylene) glycols (also known as Pluronics), polytetramethylene glycols (i.e., poly-tetrahydrofurans) or poly(ethylene-co-tetramethylene) glycols. Other examples are (b) polyesterdiols or copolyester diols, made by polycondensation of dicarboxylic acids and diols, or by polycondensation of hydroxyacids, or by ringopening polymerization of, e.g., ε-caprolactone, glycolide, lactide, δ-valerolactone, 1,4-dioxane-2-one, 1,5-dioxepan-2-one, oxepan-2,7-dione, and the like. Specific examples are poly ε-caprolactonediols, hydroxy-terminated polyadipates or polyglutarates, such as hydroxy-terminated poly(1,4-butylene adipate)s, hydroxy-terminated poly(1,2-ethylene adipate)s, hydroxy-terminated poly(1,4-butylene glutarate)s, hydroxy-terminated poly(2-methyl-1,3-propylene adipate)s, hydroxy-terminated poly(2-methyl-1,3-propylene glutarate)s, hydroxy-terminated poly(2-methyl-1,5-pentylene adipate)s, polyesterdiols of polylactides, polyglycolides, poly(lactide-co-glycolide)s, poly(hydroxy butyrate)s, polyterephthalates such as polyethyleneterephthalates and polybutyleneterephthalates, polyisophthalates (e.g., hydroxy-terminated copolymers of 5-NaSO$_3$-isophtalic acid, isophthalic acid, diethyleneglycol and bis-hydroxymethylene-cyclohexane, hydroxy-terminated copolymers of isophtalic acid and 1,4-butanediol, hydroxy-terminated copolymers of 5-NaSO$_3$-isophtalic acid, adipic acid, phthalic acid and 1,6-hexanediol) and polyphthalates such as poly(1,6-hexylene phthalate)s or hydroxy-terminated copolymers of phthalic acid and diethyleneglycol. Further examples include (c) polyolefine diols or hydrogenated polyolefine diols, such as hydroxyl-functionalized polybutadienes or hydroxyl-functionalized hydrogenated poly(ethylene-butylene)s such as Kraton L-2203 or Nisso-type materials. Other examples are (d) hydroxy-functionalized polycarbonates and co-polycarbonates based on glycols or made by ringopening polymerization of, e.g., trimethylenecarbonate, 1,3-dioxepane-2-one, 1,3-dioxanone-2-on and 1,3,8,10-tetraoxacyclotetradecane-2,9-dione. Examples are hydroxy-terminated poly(1,3-propanediol carbonate)glycols, poly(trimethylenecarbonate)s, poly(1,6-hexanediol carbonate)glycols. More examples include (e) low molecular weight diols based on dimerized fatty acids such as Pripols and Priplasts, such as Pripol 2033, Priplast 3190 or Priplast 3192 (marketed by Uniqema BV, the Netherlands), (f) polysiloxanes such as α,ω-bis(6-hydroxy hexyl) polydimethylsiloxanes, α,ω-bis(oligo-ethyleneoxide) polydimethylsiloxanes, and (g) polyamides such as α,ω-dihydroxy-polyamides and polyoxazolines. Of course, examples are also (h) alcohol-terminated co-polymers of the examples mentioned above, such as (block)-co-polymers of poly-caprolactone and ethylene glycol or (block)-co-polymers of poly-caprolactone and tetramethylene glycol.

Preferably, polymer backbone P comprises telechelic polymers of categories (a), (b), (d), and (g), more preferred are those of (a). Within category (a), the telechelic polymer is preferably selected from the group consisting of polyethylene glycol, poly(tetrahydrofuran) or poly(ethylene-co-propylene) glycol (random or block), most preferably, polyethylene glycol.

As an alternative, although less preferred, telechelic polyoxyalkylene amines may be used, such as polyethylene glycols or poly(ethylene-co-propylene) glycols with terminal amino groups. Examples are JEFFAMINES® as sold by Huntsman.

According to the second embodiment of this disclosure, the functional polymer P that is used to prepare the water gellant is from natural origin and it is selected from the group consisting of proteins (e.g., proteins selected from the group consisting of collagen, gelatine, and fibrin); polysaccharides (e.g., polysaccharides selected from the group consisting of hyaluronic acid, agar, agarose, xantham gums, natural gum, alginate, chitosan and inulin) and synthetic derivatives from these polymers of natural origin, preferably collagen or hyaluronic acid.

The Cross-Linkable Group D

The cross-linkable group D comprises a reactive group that is able to cross-link with other groups D, optionally in the presence of an auxiliary A that mediates or initiates the cross-linking, or is able to cross-link with an auxiliary A. Preferably, cross-linkable group D cross-links via an oxidative pathway mediated by auxiliary A as oxidator.

The cross-linkable group D has a molecular weight of about 70 to about 1,000, preferably about 70 to about 500, more preferably about 70 to about 250, more preferably about 70 to about 200, and most preferably about 100 to about 175 Dalton.

The cross-linkable groups D that are used to prepare the water gellant of the disclosure comprise at least one functional group F that can react with the polymer backbone P or the 4H-unit and form a chemical bond with P or the 4H-unit, and they comprise at least one reactive group Z that can cross-link with other groups Z.

It is preferred that D represents the group $(-)_x$L-Z, wherein x is 1 to 4, L is a linker moiety that is covalently linked to Z and is selected from (i) the group consisting of cyclic, linear or branched $C_1$-$C_{24}$ alkylene groups, $C_6$-$C_{24}$ arylene groups, $C_7$-$C_{24}$ alkarylene groups and $C_7$-$C_{24}$ arylalkylene groups and/or (ii) the group consisting of amino acid residues according to the formula (G):

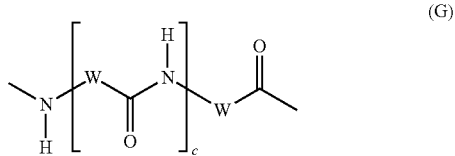

(G)

wherein W is a cyclic, linear or branched $C_1$-$C_{24}$ alkylene group and c is 0-3.

Z is preferably selected from the group consisting of multihydroxy aryl, $C_1$-$C_6$ alkyleneboronic acid, $C_6$-$C_{12}$ aryleneboronic acid, $C_7$-$C_{12}$ alkylaryleneboronic acid, $C_7$-$C_{12}$ arylalkyleneboronic acid, thiol, dithioether —S—S—$R^9$ (wherein $R^9$ is $C_1$-$C_6$ alkyl or alanyl), $C_2$-$C_6$ alkynyl, $C_2$-$C_6$ alkenyl, methacrylate or acrylate. An example of an alkylene boronic acid group is the group methylene boronic acid —$CH_2$—$B(OH)_2$. An example of a dithioether group is dithiocysteine.

According to a preferred embodiment of this disclosure, the cross-linkable component that is used to prepare the water gellant of the disclosure has the general formula (C):

$(F)_x$-L-Z           (C)

where Z represents a chemical group that can cross-link, L represents a linker moiety, and F represents the reactive group linked to the linker moiety, and x represents the number of reactive groups connected to the linker moiety that ranges from 1 to 4. Preferably, x ranges from 1 to 2, most preferably x is 1 and the cross-linkable component that is used to prepare the water gellant of the disclosure can then be represented by the following formula:

F-L-Z           (D)

F is a reactive group that can react with complementary reactive groups on P or the 4H-unit. F is selected from hydroxy, amine, thiol, isocyanate, carboxylic acid, carboxylic ester, and combinations of these end groups, and forms moieties as defined in the section "General Definitions."

Preferably, F is selected from the group consisting of hydroxy, amine, and carboxylic acid, more preferably hydroxy and amine, most preferably amine. When x is 2 or larger, F can be the same or different in one D.

Z can be any chemical group that can react with the same chemical group or with a complementary chemical group, preferably Z is a chemical group that can react with the same chemical group in the presence of an auxiliary A. Preferably, Z is selected from multihydroxy aryl (which contains 2-6 hydroxy groups, preferably 2 hydroxy groups), $C_1$-$C_6$ alkyleneboronic acid, $C_6$-$C_{12}$ aryleneboronic acid, $C_7$-$C_{12}$ alkylaryleneboronic acid, $C_7$-$C_{12}$ arylalkyleneboronic acid, thiol, dithioether —S—S—$R^9$ (wherein $R^9$ is $C_1$-$C_6$ alkyl or alanyl), $C_2$-$C_6$ alkynyl or $C_2$-$C_6$ alkenyl, methacrylate and acrylate. More preferably, Z is selected from multihydroxy aryl, $C_1$-$C_6$ alkyleneboronic acid, $C_6$-$C_{12}$ aryleneboronic acid, $C_7$-$C_{12}$ alkylaryleneboronic acid, $C_7$-$C_{12}$ arylalkyleneboronic acid, thiol, dithioether —S—S—$R^9$ (wherein $R^9$ is $C_1$-$C_6$ alkyl or alanyl) and $C_2$-$C_6$ alkynyl, most preferably multihydroxy aryl.

L is a linker moiety that is covalently linked to F and covalently linked to Z. L is selected from (i) the group consisting of cyclic, linear or branched $C_1$-$C_{24}$ alkylene groups, $C_6$-$C_{24}$ arylene groups, $C_7$-$C_{24}$ alkarylene groups and $C_7$-$C_{24}$ arylalkylene groups, wherein the alkylene groups, arylene groups, alkarylene groups and arylalkylene groups optionally, but not preferably, comprise 1-5 heteroatoms selected from the group consisting of O, N and S, and (ii) the group consisting of amino acids, protected amino acids, dipeptides, tripeptides, tetrapeptides, protected or partially protected, or a combination of (i) and (ii). The groups according to group (ii) do not necessarily comprise a reactive group F since they are already provided with an (protected) amino group and a (protected) carboxylic acid group. Preferably, L is selected from (i).

According to an embodiment, the groups according to group (ii) are preferably represented by formula (E):

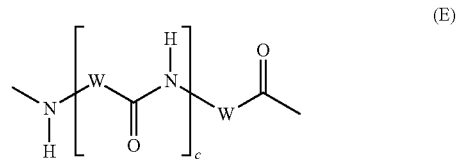

(E)

wherein W is a cyclic, linear or branched $C_1$-$C_{24}$ alkylene group and c is 0-3.

In a first preferred embodiment, the cross-linking component that is used to prepare the water gellant of the disclosure comprises a 3,4-dihydroxy aryl group as cross-linkable group Z and F is selected from amine, hydroxy, and carboxylic acid. More preferably, the cross-linking component that is used to prepare the water gellant of the disclosure is selected from dopamine, 3,4-dihydroxy cinnamic acid, 3,4-dihydroxy hydrocinnamic acid, 3,4-dihydroxy phenyl acetic acid, 3,4-dihydroxy phenyl alanine, 3-hydroxytyrosol, 3,4-dihydroxy phenyl glycol, all optionally comprising amino acid or oligopeptide residues, even more preferably from dopamine, 3,4-dihydroxy phenyl alanine, and 3,4-dihydroxy phenyl alanine that optionally comprises oligopeptides.

In a second preferred embodiment, the cross-linking component that is used to prepare the water gellant of the disclosure comprises a thiol group as cross-linkable group Z and F is selected from amine, hydroxyl, and carboxylic acid. More preferably, the cross-linking component that is used to prepare the water gellant of the disclosure is selected from α,ω-mercapto alkyl amines, α,ω-mercapto alkyl alcohols, α,ω-mercapto carboxylic acids, and cysteine derivatives, in which the mercapto-group is optionally present as a thiouronium group, even more preferably selected from cysteamine, cysteine, 2-mercapto ethanol, 3-mercapto propanol, 6-mercapto hexanoic acid, 12-mercapto dodecanoic acid, and cysteine-comprising oligopeptides.

In a third preferred embodiment, the cross-linking component that is used to prepare the water gellant of the disclosure comprises an alkynyl, alkenyl or acrylate as cross-linkable group Z, and F is selected from amine, hydroxyl, and carboxylic acid. Most preferably, Z is alkynyl in this embodiment. Preferably, the alkynyl and alkenyl groups are $C_2$-$C_{24}$ alkynyl and $C_2$-$C_{24}$ alkenyl groups.

The Liquid Aqueous Formulation

The liquid aqueous formulation comprises the water gellant dissolved in water. The amount of the water gellant in the liquid aqueous formulation ranges from about 0.3%-50.0% by weight, preferably from about 1%-25% by weight, more preferably from about 1%-20% by weight, more preferably from about 2%-10% by weight, and most preferably from about 2%-3% by weight, based on the total weight of the liquid aqueous formulation. The liquid aqueous formulation may contain additional functional ingredients that will contribute to the specific use of the hydrogel.

The liquid aqueous formulation comprises about 50.0-99.7 wt. % of water, preferably about 75-99% by weight, more preferably about 80-99 wt. %, and most preferably about 90-98 wt. %, based on the total weight of the liquid aqueous formulation. Preferably, the water contains a pH-buffer known in the art, such as a PBS or borate buffer.

Preferably, the pH of the liquid aqueous formulation is in between pH of about 6 and pH of about 11, more preferably in between pH of about 7 and pH of about 9, most preferably in between pH of about 7 and pH of about 8.

The viscosity of the liquid aqueous formulation is low enough to allow administration of the formulation by a syringe or catheter. Consequently, the liquid aqueous formulation is not gelled as determined with a simple inverted vial test. More preferably, the loss factor (tan δ) at 1 Hz and 37° C. as determined with a plate-plate rheometer is about 0.7 or higher, most preferably the loss factor is higher than about 1.0.

In another preferred embodiment, the dynamic viscosity of the liquid aqueous formulation at 25° C. is about 0.01 to about 10 Pa·s, preferably of about 0.1 to about 8 Pa·s, most preferably of about 0.8 to about 5 Pa·s, as measured with a rotational viscometer.

Obviously, but not preferably, the liquid aqueous formulation may contain other polar solvents, preferably those solvents having a dielectric constant ε at 20° C. of at least about 20. The upper limit is given by the dielectric constant ε at 20° C. for pure water, which is about 80 (*Handbook of Chemistry & Physics*, 59$^{th}$ Ed., page E-61, 1978-1979). Suitable examples are DMSO, alcohols, preferably ethanol, glycols, and glycerols. Preferably, ethanol, glycol, propyleneglycol, and glycerol. Preferably, the amount of other solvents is lower than about 15% by weight, more preferably lower than about 8% by weight, and most preferably lower than about 0.1% by weight, calculated on the basis of the total weight of the liquid aqueous formulation.

In another preferred embodiment, the liquid aqueous formulation comprises an additional polymer in order to modify the rheological properties of the liquid aqueous formulation. This additional polymer is hydrophilic and may represent any type of polymer backbone known in the art, preferably polyethers, polyesters, polyamides, polyoxazolines, polyamines, polyacrylates, polymethacrylates, polyolefins, hydrogenated polyolefins, polysiloxanes, polycarbonates, (per)fluorinated polyethers, polyvinylenes, or co-polymers of such polymers. More preferably, the polymer backbone is a polyether, polyester, polyacrylate, polymethacrylate, polyolefin, hydrogenated polyolefin, polycarbonate, polyvinylene, or a co-polymer of such polymers. Even more preferred are polyethers, polyesters, or copolymers thereof. Most preferably, this additional polymer is a polyether, preferably a polyglycol, preferably a polyethylene glycol or a poly ethylene-co-propylene glycol (random or block), most preferably a polyethylene glycol.

This additional polymer preferably is a supramolecular polymer that comprises at least one 4H-unit. These polymers and their aqueous formulation are in detail disclosed in WO 2006/118460 and EP 1972661 A1, which are incorporated by reference herein. The amount of additional polymer is in the range of about 0% to 990% by weight of the total solids content, preferably about 1% to 90% by weight, most preferably about 1% to 50% by weight of the total solids content of the liquid aqueous formulation.

The liquid aqueous formulation may comprise additional ingredients selected from a solid filler, a diluent, a thickener, a carrier, and an excipient known in the art. A non-limited list of additional ingredients includes sugars, starches, cellulose and its derivatives, gelatin, talc, clays, waxes (natural and synthetic), oils from natural origin, fatty acids and their esters, and ionic additives. Preferably, clay particles are added to improve the hydrogel properties. Clay particles may be selected from laponite and bentonite, optionally in the presence of (ionic) compatibilizers known in the art.

In another embodiment, the liquid aqueous formulations comprise a biologically active or pharmaceutically active compound. The liquid aqueous formulation may also comprise a bioactive species, e.g., a living cell, an enzyme, or a micro-organism. A living cell in this embodiment means and includes individual animal and plant cells, cell clusters, tissues, organs and organisms, including organisms such as bacteria, fungi or molds. A biologically active or pharmaceutically active compound, as used herein, includes a compound that provides a therapeutic, diagnostic or prophylactic effect, a compound that affects or participates in tissue growth, cell growth, cell differentiation, a compound that may be able to invoke a biological action such as an immune response, or could play any other role in one or more biological processes. Such compounds, peptide or non-peptide, protein or non-protein, include, but are not limited to, antimicrobial agents (including antibacterial, hemotherapeutic and anti-fungal agents), anti-viral agents, anti-tumor agents, hormones, hormone antagonistics, corticosteroids such as mineralocorticosteroids or glucocorticosteroids, androgents, estrogens, progestins immunogenic agents, anti-inflammatory agents, anti-gout agents, centrally acting analgesics, local anesthetics, centrally active muscle relaxants, growth factors, fluorescent dyes, contrast agents, nucleic acids, DNA-derivatives, RNA-derivatives, lipids, lipopolysaccharides, (poly)saccharides, vitamins, and peptides, polypeptides and proteins in general. In this embodiment, preferably, the biologically active compounds comprise at least one 4H-unit up to a maximum of ten 4H-units, preferably one to four, and most preferably two to four 4H-units. These 4H-units are covalently attached to the biologically active compound.

Apart from the previous list, it is also possible to load the liquid aqueous formulations with inorganic compounds, such as reactive oxygen scavengers and bone-extracts like apatite.

It is possible within the scope of this disclosure to incorporate drugs of a polymeric nature, but also to incorporate drugs or vitamins of a relatively small molecular weight of less than about 1500, or even less than about 500.

Additionally, two or more different biologically active compounds may be present in the liquid aqueous formulations. This is especially beneficial when the bioactivity is based on multivalent and/or synergistic interactions. A non-limiting example of such interaction is that cell adhesion is advantageously mediated by a combination of RGD and PHSRN peptides.

In a preferred embodiment of this disclosure, the liquid aqueous formulation comprises an auxiliary A that initiates or mediates the cross-linking reaction of the D groups in the water gellant. These auxiliaries A can be any species that initiates or mediates chemical reactions with groups Z. Preferably, A is selected from oxidators, radical initiators, redox-active compounds, metal salts, metalloid-containing oxyanions, acids and bases, Lewis-acids, Lewis-bases, or a combination of these auxiliaries. A typical molar ratio of A to D is in between 0.01 to 2.0 (A to D), a preferred molar ratio is in between 0.4 to 1.0 (A to D).

In a first preferred embodiment of this embodiment, A is an oxidant or initiator selected from alkali metal periodates (wherein the alkali metal is lithium, sodium, potassium rubidium or cesium), alkaline earth metal periodates (wherein the alkaline earth metal is magnesium, calcium or barium), hydrogen peroxide, organic peroxides ($R^{10}$—O—O—$R^{10}$), hydroperoxides ($R^{10}$—O—O—H) and peroxycarboxylic acids ($R^{10}$—C(O)—O—O—H) wherein $R^{10}$ is independently selected from the group of linear, branched or cyclic $C_1$-$C_{12}$ alkyl groups, $C_6$-$C_{12}$ aryl groups, $C_7$-$C_{14}$ alkaryl groups, $C_7$-$C_{14}$ arylalkyl groups and mixtures thereof, salts of a transition metal (wherein the transition metal is selected from the elements defined by Groups 3 to 12 and Period 4 to 6 of the Periodic Table and wherein the salt anion is preferably chloride), oxygen, inorganic bases (preferably hydroxides from the alkali metals and the alkali earth metals defined above), peroxidases (wherein the peroxidase is selected from the group consisting of horseradish peroxidase, cytochrome c peroxidase, glutathione peroxidase and catalase) and oxidases (wherein the oxidase is selected from the group consisting of glucose oxidase, cytochrome P450 oxidase and laccase), most preferably sodium periodate, hydrogen peroxide, oxygen, iron(III)chloride, and horseradish peroxidase.

In a second preferred embodiment of this embodiment, A is a cross-linker or initiator comprising two or more reactive groups selected from boronic acids according to the formula $R^{10}$—B(OH)$_2$, thiols according to the formula $R^{10}$—SH, thioesters according to the formula $R^{10}$—C(O)—S$R^{10}$, transition metal complexes (the transition metals are preferably selected from the group defined for the transition metal salts, most preferably iron(III)chloride or manganese(III)chloride), $C_4$-$C_{24}$ dienes and organic azides according to the formula $R^{10}$—$N_3$.

The Hydrogel

The composition of the hydrogel is identical to that of the liquid aqueous formulation, provided that the water gellant is in a cross-linked state. The amount of the cross-linked water gellant in the hydrogel ranges from about 0.3%-50.0% by weight, preferably from about 1%-25% by weight, more preferably from about 1%-20% by weight, yet more preferably from about 1%-10% by weight, and most preferably from about 2%-3% by weight, based on the total weight of the hydrogel. The hydrogel may contain additional functional ingredients that will contribute to the specific use of the hydrogel.

The hydrogel comprises about 50.0-99.7 wt. % of water, preferably about 75-99% by weight, more preferably 80-99 wt. %, yet more preferably 90-99% by weight and most preferably 97 to 98 wt. %, based on the total weight of the hydrogel.

Obviously, but not preferably, the hydrogel may contain other polar solvents, preferably those solvents having a dielectric constant c at 20° C. of at least about 20. The upper limit is given by the dielectric constant ε at 20° C. for pure water, which is about 80 (*Handbook of Chemistry & Physics*, 59$^{th}$ Ed., page E-61, 1978-1979). Suitable examples are DMSO, alcohols, and preferably ethanol, glycols, propyleneglycol and glycerols. Preferably, the amount of other solvents is lower than about 15% by weight, more preferably lower than about 8% by weight, and most preferably lower than about 0.1% by weight, calculated on the basis of the total weight of the hydrogel.

The hydrogels according to this disclosure have a limited amount of cross-links, preferably the molecular weight per cross-link is higher than about 3,000 Da, more preferably higher than about 4,000, most preferably higher than about 5,000 Da.

The hydrogels according to this disclosure have a wide range of mechanical properties, ranging from elastic to tough, depending on the nature of the polymer backbone P, the nature of the cross-linker D, and the number of 4H-units attached to the polymer. In the preferred case of elastic hydrogels, the hydrogel materials preferably have an elongation at break at 25° C. greater than about 100%, more preferably greater than about 300%, more preferably greater than about 600%. In another preferred case of elastic hydrogels, the hydrogel materials preferably have Young's modulus in between about 1 kPa to about 1 MPa, more preferably in between about 10 kPa to about 200 kPa, and most preferably in between about 20 kPa to about 100 kPa.

The hydrogels according to this disclosure can be prepared by three different methods: (i) the liquid aqueous formulation comprising the auxiliary A is administered to the desired location and the hydrogel is formed in time; (ii) the liquid aqueous formulation is in situ mixed with the auxiliary A resulting in the formation of the hydrogel; (iii) the liquid aqueous formulation is administered to the desired location and the hydrogel is formed in time; (iv) the liquid aqueous formulation is in situ mixed with another liquid aqueous formulation resulting in the formation of the hydrogel. For methods (i) and (iii), slower cross-linking reactions are preferred than for methods (ii) and (iv). Preferably, for methods (i) and (iii), the hydrogel is formed in between about 0.1 minutes and about 60 minutes, more preferably in between about 2 minutes and about 30 minutes, most preferably in between about 4 minutes and about 25 minutes. Whereas, for methods (ii) and (iv), the hydrogel is preferably formed in between about 0.05 minutes and about 10 minutes, more preferably in between about 0.1 minutes and about 5 minutes, and most preferably in between about 0.2 minutes and about 3 minutes.

Administration of the liquid formulation to the location where the hydrogels needs to be formed can be done by any method in the art, preferably selected from injection through a needle, injection through a catheter, injection through a double chamber syringe, injection through a double chamber catheter, spraying, foaming, or pouring.

The hydrogels according to this disclosure preferably show only a limited amount of swelling due to water absorption. The increase in weight of the gel due to absorption of water after 2 days at 37° C. is preferably less than about 500%, more preferably less than about 300%, and most preferably less than about 250%.

The hydrogels preferably keep their structural integrity and will not dissolve or fall apart into small fragments, upon exposure to an excess amount of water after 2 days at 37° C.

The hydrogel may comprise additional ingredients such as those listed for the liquid aqueous formulation. In a preferred embodiment, the hydrogel comprises a biologically active or pharmaceutically active compound as set out for the liquid aqueous formulation.

The hydrogels according to the disclosure show preferably adhesive properties to tissue, skin, and keratin-containing materials. More preferably, these hydrogels have a mean lap-shear tensile strength of at least about 10 kPa, more preferably, at least about 40 kPa, and most preferably at least about 50 kPa, using porcine skin as substrates and having a hydrogel solids content of about 15% by weight in PBS.

In a preferred embodiment of this disclosure, the water gellant, the liquid aqueous formulation and the hydrogel, are used in biomedical applications, such as carriers for the controlled release of drugs, scaffolds for tissue-engineering, prosthetic intervertebral disc nucleus, cardio-vascular structures, non-fouling surfaces, wound dressings and wound care, artificial cartilage material, tissue adhesion, tissue sealant, cardiac patch, transdermal patch, (adhesive) coatings for medical devices, such as water absorbers, gelators, and as thickeners for aqueous solvents. In another preferred embodiment of this disclosure, the water gellant, the liquid aqueous formulation and the hydrogel, are used in cosmetic applications, such as formulations used for skin care, make-up, hair care, deodorants and anti-perspirants.

EXAMPLES

The following examples further illustrate the preferred embodiments of the disclosure. When not specifically mentioned, chemicals are obtained from Sigma Aldrich. IPDI is isophorone diisocyanate, HMDI is methylene dicyclohexane 4,4-diisocyanate, DBTDL is dibutyl tin dilaurate, and DIPEA is diisopropylethylamine. SEC is performed with a GPC-system equipped with a KD-804 column (Showa Denko, 500-400000 Da) using RI detection with DMF comprising 10 mM LiBr as eluent at a flow rate of 1.0 mL/minute. $M_n$ and $M_w$ are calculated on selected peak relative to PEG-standards (Polymer Laboratories, molecular weight range: 580-100000 g/mol).

Polymer 1

Telechelic hydroxy-terminated PEG-3000 (16.0 g, 5.33 mmol) was heated in vacuo in a 3-neck flask to 120° C., together with 2-amino-4-hydroxy-5-(2-hydroxy ethyl)-6-methyl-pyrimidine (676 mg, 4.00 mmol) and stirred for 1 hour in vacuo. After cooling to 70° C., IPDI (2.37 g, 10.7 mmol) was added and 1 drop DBTDL while stirring. After 1 hour, the reaction mixture was stirred for another 2 hours at 120° C., followed by cooling to 100° C. under an argon atmosphere. Subsequently, dopamine hydrochloride (557 mg, 2.93 mmol) was dissolved in 2 mL DMSO in the presence of 0.55 mL DIPEA, and added to the viscous reaction mixture at 100° C. The mixture was stirred for 15 minutes at 100° C., followed by cooling to 70° C. while stirring under an argon atmosphere. To this mixture, 30 mL methyl-THF was added, followed by cooling and stirring until 25° C., after which, 30 mL methyl-t-butyl ether was added, resulting in the formation of a white precipitate, which was isolated by filtration. The dried precipitate was redissolved in 60 mL chloroform and 7 mL ethanol, filtered, and precipitated by the addition of methyl-t-butyl ether. The product was isolated by filtration and subsequent drying of the residue. Yield: 87%. SEC: $M_n$=5.0 kDa.

Polymer 2

Telechelic hydroxy-terminated PEG-6000 (31.6 g, 5.27 mmol) was heated in vacuo in a 3-neck flask to 120° C., together with 2-amino-4-hydroxy-5-(2-hydroxy ethyl)-6-methyl-pyrimidine (455 mg, 2.69 mmol) and stirred for 1 hour in vacuo. After cooling to 70° C., IPDI (2.34 g, 10.53 mmol) was added and 1 drop DBTDL while stirring. After 1 hour, the reaction mixture was stirred for another 2 hours at 120° C., followed by cooling to 100° C. under an argon atmosphere. Subsequently, dopamine hydrochloride (1.10 g, 5.79 mmol) was dissolved in 7 mL DMSO in the presence of 1.1 mL DIPEA, and added to the viscous reaction mixture at 100° C. The mixture was stirred for 15 minutes at 100° C., followed by cooling to 70° C. while stirring under an argon atmosphere. To this mixture, 50 mL methyl-THF was added, followed by cooling and stirring until 25° C., after which, 50 mL methyl-t-butyl ether was added, resulting in the formation of a white precipitate, which was isolated by filtration. The dried precipitate was redissolved in 80 mL chloroform and 10 mL ethanol, filtered, and precipitated by the addition of methyl-t-butyl ether. The product was isolated by filtration and subsequent drying of the residue. Yield: 91%. SEC: $M_n$=9.0 kDa.

Polymer 3

Telechelic hydroxy-terminated PEG-6000 (22.8 g, 3.80 mmol) was heated in vacuo in a 3-neck flask to 120° C., together with 2-amino-4-hydroxy-5-(2-hydroxy ethyl)-6-methyl-pyrimidine (425 mg, 2.51 mmol) and stirred for 1 hour in vacuo. After cooling to 80° C., HMDI (1.99 g, 7.59 mmol) was added and 1 drop DBTDL while stirring. After 1 hour, the reaction mixture was stirred for another 2 hours at 130° C., followed by cooling to 100° C. under an argon atmosphere. Subsequently, dopamine hydrochloride (0.48 g, 2.53 mmol) was dissolved in 2 mL DMSO in the presence of 0.5 mL DIPEA, and added to the viscous reaction mixture at 100° C. The mixture was stirred for 15 minutes at 100° C., followed by cooling to 70° C. while stirring under an argon atmosphere. To this mixture, 30 mL methyl-THF was added, followed by cooling and stirring until 25° C., after which, 30 mL methyl-t-butyl ether was added resulting in the formation of a white precipitate, which was isolated by filtration. The dried precipitate was redissolved in 60 mL chloroform and 7 mL ethanol, filtered, and precipitated by the addition of methyl-t-butyl ether. The product was isolated by filtration and subsequent drying of the residue. Yield: 86%. SEC: $M_n$=12 kDa.

Polymer 4

Telechelic hydroxy-terminated PEG-10000 (25.0 g, 2.50 mmol) was heated in vacuo in a 3-neck flask to 120° C., together with 2-amino-4-hydroxy-5-(2-hydroxy ethyl)-6-methyl-pyrimidine (280 mg, 1.66 mmol) and stirred for 1 hour in vacuo. After cooling to 80° C., HMDI (1.31 g, 4.99 mmol) was added and 1 drop DBTDL while stirring. After 1 hour, the reaction mixture was stirred for another 2 hours at 130° C., followed by cooling to 100° C. under an argon atmosphere. Subsequently, dopamine hydrochloride (0.35 g, 1.84 mmol) was dissolved in 1.5 mL DMSO in the presence of 0.35 mL DIPEA, and added to the viscous reaction mixture at 100° C. The mixture was stirred for 15 minutes at 100° C., followed by cooling to 70° C. while stirring under an argon atmosphere. To this mixture, 30 mL methyl-THF was added, followed by cooling and stirring until 25° C., after which, 30 mL methyl-t-butyl ether was added, resulting in the formation of a white precipitate, which was isolated by filtration. The dried precipitate was redissolved in 80 mL chloroform and 10 mL ethanol, filtered, and precipitated by the addition of methyl-t-butyl ether. The product was isolated by filtration and subsequent drying of the residue. Yield: 86%. SEC: $M_n$=21 kDa.

Polymer 5

Telechelic hydroxy-terminated PEG-6000 (10.0 g, 1.67 mmol) was heated in vacuo in a 3-neck flask to 120° C., together with 2-amino-4-hydroxy-5-(2-hydroxy ethyl)-6-methyl-pyrimidine (211 mg, 1.25 mmol) and stirred for 1 hour in vacuo. After cooling to 70° C., IPDI (0.74 g, 3.33 mmol) was added and 1 drop DBTDL while stirring. After 1 hour, the reaction mixture was stirred for another 2 hours at 120° C., followed by cooling to 80° C. under an argon atmosphere. Subsequently, 2-(2-aminoethyl)isothiourea dihydrobromide (234 mg, 0.83 mmol) was dissolved in 2 mL DMSO in the presence of 0.3 mL DIPEA, and added to the viscous reaction mixture at 80° C. The mixture was stirred for 60 minutes at 80° C., followed by cooling to 60° C. while stirring under an argon atmosphere. To this mixture, 50 mL methyl-THF and 10 mL ethanol were added, followed by cooling and stirring until 25° C., after which, 100 mL methyl-t-butyl ether was added, resulting in the formation of a white precipitate, the product was isolated by filtration and subsequent drying of the residue. Yield: 79%. SEC: $M_n$=9.3 kDa.

Polymer 6

Telechelic hydroxy-terminated PEG-6000 (12.6 g, 2.11 mmol) was heated in vacuo in a 3-neck flask to 120° C. and stirred for 1 hour in vacuo. After cooling to 70° C., IPDI (0.94 g, 4.23 mmol) was added and 1 drop DBTDL while stirring. After 1 hour, the reaction mixture was stirred for another 1 hour at 80° C. Subsequently, 1,6-diaminohexane (122 mg, 1.06 mmol) and dopamine hydrochloride (440 mg, 2.32 mmol) were dissolved in 2 mL DMSO in the presence of 0.3 mL DIPEA, and added to the viscous reaction mixture at 80° C. The mixture was stirred for 60 minutes at 80° C., followed by cooling to 60° C. while stirring under an argon atmosphere. To this mixture, 50 mL methyl-THF and 50 mL ethanol were added, followed by cooling and stirring until 25° C., after which, 100 mL methyl-t-butyl ether was added resulting in the formation of a white precipitate, the product was isolated by filtration and subsequent drying of the residue. Yield: 92%. SEC: $M_n$=11 kDa.

Comparative Polymer 1

Comparative Polymer 1 is a linear polymer with only 4H units according to WO 2006/118460.

Telechelic hydroxy-terminated PEG-6000 (100 g, 16.7 mmol) was heated in vacuo in a 3-neck flask to 120° C., together with 2-amino-4-hydroxy-5-(2-hydroxy ethyl)-6-methyl-pyrimidine (2.46 g, 14.6 mmol) and stirred for 2 hours in vacuo. After cooling to 80° C., HMDI (8.75 g, 33.4 mmol) was added and 2 drops DBTDL while stirring. After 1 hour, the reaction mixture was stirred for another 2 hours at 120° C., followed by putting it in an oven at 145° C. in vacuo for 45 minutes, after which it was collected and the product was isolated as a solid polymer at room temperature. Yield: 96%. SEC: $M_n$=24 kDa.

Comparative Polymer 2

Comparative Polymer 2 is a linear cross-linkable polymer with no 4H units.

Telechelic hydroxy-terminated PEG-6000 (10.5 g, 1.75 mmol) was heated in vacuo in a 3-neck flask to 120° C. and stirred for 1 hour in vacuo. After cooling to 70° C., IPDI (583 mg, 2.62 mmol) was added and 1 drop DBTDL while stirring. After 1 hour, the reaction mixture was stirred for another 1 hour at 110° C., followed by cooling to 100° C. under an argon atmosphere. Subsequently, dopamine hydrochloride (366 mg, 1.93 mmol) was dissolved in 3 mL DMSO in the presence of 0.35 mL DIPEA, and added to the viscous reaction mixture at 100° C. The mixture was stirred for 15 minutes at 100° C., followed by cooling to 70° C. while stirring under an argon atmosphere. To this mixture, 50 mL methyl-THF was added, followed by cooling and stirring until 25° C., after which, 50 mL methyl-t-butyl ether was added, resulting in the formation of a white precipitate, which was isolated by filtration. The dried precipitate was redissolved in 80 mL chloroform and 10 mL ethanol, filtered, and precipitated by the addition of methyl-t-butyl ether. The product was isolated by filtration and subsequent drying of the residue. Yield: 91%. SEC: $M_n$=7.2 kDa.

Aqueous Liquid Formulations

Aqueous solutions were obtained by dissolving the desired amount of polymer into deionized water or into standard PBS buffer solution at pH=7.4. Table 1 lists typical formulations obtained with the polymers of the examples.

TABLE 1

Liquid Aqueous Formulations

| Formulation | Material | Solids content | Medium | Morphology |
| --- | --- | --- | --- | --- |
| 1 | Polymer 1 | 15 wt % | H₂O | liquid |
| 2 | Polymer 1 | 20 wt % | H₂O | liquid |
| 3 | Polymer 2 | 5 wt % | PBS | liquid |
| 4 | Polymer 3 | 5 wt % | H₂O | liquid |
| 5 | Polymer 3 | 10 wt % | H₂O | liquid |
| 6 | Polymer 3 | 15 wt % | H₂O | viscous liquid |
| 7 | Polymer 4 | 10 wt % | H₂O | viscous liquid |
| 8 | Polymer 5 | 10 wt % | H₂O | liquid |
| 9 | Comparative Polymer 1 | 5 wt % | PBS | elastic gel |
| 10 | Comparative Polymer 2 | 5 wt % | PBS | liquid |
| 11 | Comparative Polymer 2 | 5 wt % | H₂O | liquid |
| 12 | Comparative Polymer 2 | 10 wt % | H₂O | liquid |
| 13 | Polymer 6 | 5 wt % | PBS | liquid |
| 14 | Polymer 6 | 10 wt % | PBS | liquid |
| 15 | Polymer 6 | 20 wt % | PBS | liquid |

Formulations 1 to 8 and 13 to 15 of Polymers 1 to 6 and formulations 10 to 12 of Comparative Polymer 2 can be injected with a syringe. Formulation 9 of Comparative Polymer 1 is an elastic gel due to the high level of 4H-units and, therefore, cannot be pushed through a syringe.

Hydrogel

The hydrogels were obtained after cross-linking the selected liquid aqueous formulations from Table 1 by addition of aqueous $NaIO_4$ solutions, following method A or B, as depicted in Table 2. Hydrogels were formed in timeframes ranging from a few minutes to half an hour.

Method A: $NaIO_4$ is dissolved in 0.01 M NaOH in concentrations determined by the amount of mol equivalents to be added (typically 0.1 to 0.3 M). The added volume of the $NaIO_4$ solution is 20/o of the volume of the formulation to be cross-linked. After addition of the $NaIO_4$-solution via a syringe, the mixture is vortexed for 10 seconds and left standing.

Method B: $NaIO_4$ is dissolved in $H_2O$ in concentrations determined by the amount of mol equivalents to be added (typically 0.03 M). The added volume of the $NaIO_4$ solution is 20% of the volume of the formulation to be cross-linked. After addition of the $NaIO_4$-solution via a syringe, the mixture is vortexed for 10 seconds and left standing.

TABLE 2

Hydrogels

| Hydrogel | Formulation | Molequiv. NaIO₄ | Method | Morphology |
| --- | --- | --- | --- | --- |
| 1 | 1 | 2.0 | A | elastic gel after 15' |
| 2 | 2 | 2.0 | A | elastic gel after 25' |
| 3 | 3 | 0.8 | B | elastic gel after 4' |
| 4 | 4 | 2.0 | A | elastic gel after 20' |
| 5 | 4 | 2.0 | A | elastic gel after 5' |
| 6 | 7 | 2.0 | A | elastic gel after 3' |
| 7 | 10 | 0.8 | B | liquid[a] |
| 8 | 11 | 2.0 | A | liquid[a] |
| 9 | 12 | 2.0 | A | liquid[a] |
| 10 | 13 | 1.0 | B | elastic gel after 6' |
| 12 | 14 | 1.0 | B | elastic gel after 7' |
| 13 | 15 | 1.0 | B | elastic gel after 8' |

[a]these formulations did not gel and remained a liquid for at least 10 hours after addition of the NaIO₄ solutions, revealing that the 4H-units are necessary to obtain a hydrogel.

Tensile Performance Hydrogels

Dog bones (22 mm) were cut from films of the hydrogels obtained after 16 hours of curing in a Teflon mold in an environment saturated with water vapor; typical thicknesses were 3-5 mm. After cutting of the dog bones, they were directly measured in order to prevent significant water evaporation. Tensile testing took place at room temperature with a cross-head speed of 20 mm/minute. Results are depicted in Table 3.

TABLE 3

Tensile performance of the hydrogels

| Hydrogel | Emod | Tensile strength | Elongation at break |
|---|---|---|---|
| 1 | 23 kPa | 98 kPa | 750% |
| 2 | 28 kPa | 77 kPa | 376% |

Self Healing of the Hydrogels

A circular film with a thickness of 3 mm and a diameter of 25 mm cut from hydrogel 2 was mounted on a 3-necked flask and subjected to a water pressure of 150 mm Hg. The hydrogel seal did not show any leakage. After punching this hydrogel seal with an injection needle (20 G), no leakage was observed after removal of the needle. Moreover, punching this hydrogel seal with a scalpel did also not result in leakage after removal of the blade from the hydrogel. Clearly, the freshly created surface shows sufficient self-adhesion to close punctures and withstand a load of 0.2 bar.

The invention claimed is:

1. A water gellant comprising a hydrophilic polymer backbone P, a cross-linkable group D that is able to cross-link with other groups D and a 4H-unit 4H, having the structure according to formula (A) or formula (B) or formula (C):

$$D\text{-}[(4H)]_b\text{---}[P\text{-}(4H)]_n\text{---}[P]_a\text{-}D \qquad (A)$$

or $$\{\text{-}(4H)_b\text{---}[P\text{-}(4H)]_n\text{---}[P]_a\text{-}D\text{-}\}_q \qquad (B)$$

or $$\{\text{-}[4H]_n\text{---}[P\text{-}D]_q\text{-}\} \qquad (C)$$

wherein:
n is in the range of 1 to 10;
a is 0 or 1;
b is 0 or 1;
q is in the range of 1 to 10;
D represents the group L-Z, wherein L is a linker moiety that is covalently linked to Z and is selected from (i) the group consisting of cyclic, linear or branched $C_1$-$C_{24}$ alkylene groups, $C_6$-$C_{24}$ arylene groups, $C_7$-$C_{24}$ alkarylene groups and $C_7$-$C_{24}$ arylalkylene groups and/or (ii) the group consisting of amino acid residues according to the formula (G):

$$\text{(G)}$$

wherein W is a cyclic, linear or branched $C_1$-$C_{24}$ alkylene group;
c is 0-3;
Z is an aryl group that contains 2 to 6 hydroxy groups or Z is a thiol group;

4H represents the 4H-unit that has the general formula (3) or formula (4) and tautomers thereof:

$$\text{(3)}$$

$$\text{(4)}$$

wherein X is nitrogen atom or a carbon atom bearing a substituent $R^8$ and wherein $R^1$, $R^2$, $R^3$ and $R^8$ are independently selected from the group consisting of:
(a) hydrogen;
(b) $C_1$-$C_{20}$ alkyl;
(c) $C_6$-$C_{12}$ aryl;
(d) $C_7$-$C_{12}$ alkaryl;
(e) $C_7$-$C_{12}$ alkylaryl;
(f) polyester groups having the formula (5)

$$\left[(CR^4{}_2)_n\text{---}\underset{\underset{O}{\|}}{C}\text{---}O\right]_m\text{---}Y \qquad (5)$$

wherein $R^4$ and Y are independently selected from the group consisting of hydrogen and $C_1$-$C_6$ linear or branched alkyl, n is 1-6 and m is 10 to 100;
(g) $C_1$-$C_{10}$ alkyl groups substituted with 1-4 ureido groups according to the formula (6)

$$R^5\text{---}NH\text{---}C(O)\text{---}NH\text{---} \qquad (6)$$

wherein $R^5$ is selected from the group consisting of hydrogen and $C_1$-$C_6$ linear or branched alkyl;
(h) polyether groups having the formula (7)

$$\text{---}[CR^6H\text{---}CR^7H\text{---}O]_o\text{---}Y \qquad (7)$$

wherein Y, $R^6$ and $R^7$ are independently selected from the group consisting of hydrogen and $C_1$-$C_6$ linear or branched alkyl and o is 10-100; and
wherein the 4H-unit is bonded to the polymer backbone P via $R^1$ and $R^2$ while $R^3$ represents a side chain according to (a)-(h), or via $R^1$ and $R^3$ while $R^2$ represents a side chain according to (a)-(h).

2. The water gellant according to claim 1, wherein the polymer backbone P is selected from the group consisting of telechelic polymers and natural polymers.

3. The water gellant according to claim 1, wherein the water gellant has a number average molecular weight of 1,000 to 60,000.

4. The water gellant according to claim 1, wherein the polymer backbone P is selected from the group consisting of polyether, polyester, polycarbonate, and a copolymer of any thereof.

5. The water gellant according to claim 1, wherein the water gellant has a linear structure according to formula (A).

6. A process for preparing the water gellant of claim 1, said process comprising reacting a polymer component P—(F)$_v$, a 4H-unit 4H—(F)$_w$ and a cross-linking component (F)$_x$-L-Z, wherein:
- F represents a reactive end-group selected from the group consisting of hydroxy, amine, thiol, isocyanate, carboxylic acid, carboxylic ester, and combinations of these end groups;
- v is in the range of 1-4;
- w is in the range of 1-4;
- L represents a linker moiety that is covalently linked to Z and is selected from (i) the group consisting of cyclic, linear or branched $C_1$-$C_{24}$ alkylene groups, $C_6$-$C_{24}$ arylene groups, $C_7$-$C_{24}$ alkarylene groups and $C_7$-$C_{24}$ arylalkylene groups and/or (ii) the group consisting of amino acid residues according to the formula (G):

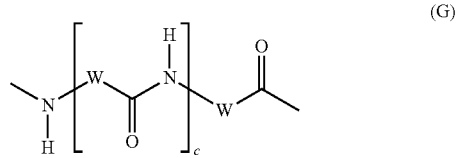

(G)

wherein W is a cyclic, linear or branched $C_1$-$C_{24}$ alkylene group;
c is 0-3; and
Z represents a group that can cross-link and is selected from a thiol group and an aryl group that contains 2 to 6 hydroxy groups.

7. A process for preparing the water gellant of claim 1, said process comprising reacting a polymer component P—(F)$_v$, a precursor of the 4H-unit according to the formula 4H*—(F)$_w$ and a cross-linking component (F)$_x$-L-Z, wherein:
4H*—(F)$_w$ is represented by formula (11) or formula (12):

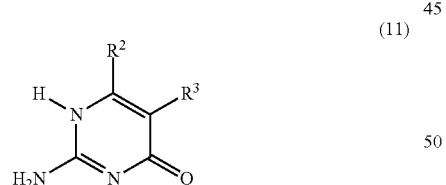

(11)

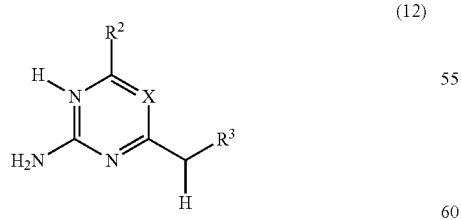

(12)

wherein $R^2$, $R^3$ and X have the meaning as defined in claim 1;
F represents a reactive end-group selected from the group consisting of hydroxy, amine, thiol, isocyanate, carboxylic acid, carboxylic ester, and combinations of these end groups;
v is in the range of 1-4;
w is in the range of 1-4;
L represents a linker moiety that is covalently linked to Z and is selected from (i) the group consisting of cyclic, linear or branched $C_1$-$C_{24}$ alkylene groups, $C_6$-$C_{24}$ arylene groups, $C_7$-$C_{24}$ alkarylene groups and $C_7$-$C_{24}$ arylalkylene groups and/or (ii) the group consisting of amino acid residues according to the formula (G):

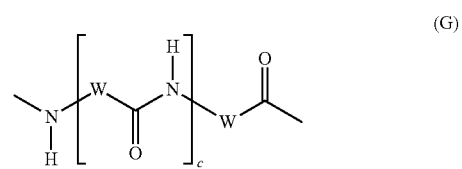

(G)

wherein W is a cyclic, linear or branched $C_1$-$C_{24}$ alkylene group;
c is 0-3; and
Z represents a group that can cross-link and is selected from a thiol group and an aryl group that contains 2 to 6 hydroxy groups.

8. The process according to claim 6, wherein the cross-linking component is dopamine.

9. A water gellant produced by a process comprising:
reacting a polymer component P—(F)$_v$, a precursor of the 4H-unit according to the formula 4H*—(F)$_w$ and a cross-linking component (F)$_x$-L-Z, wherein:
4H*—(F)$_w$ is represented by formula (11) or formula (12):

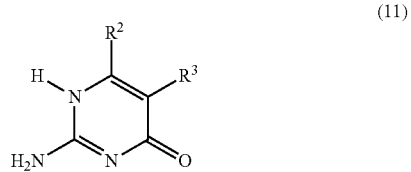

(11)

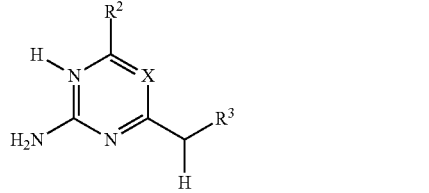

(12)

wherein X is nitrogen atom or a carbon atom bearing a substituent $R^8$ and wherein $R^1$, $R^2$, $R^3$ and $R^8$ are independently selected from the group consisting of:
(g) hydrogen;
(h) $C_1$-$C_{20}$ alkyl;
(i) $C_6$-$C_{12}$ aryl;
(j) $C_7$-$C_{12}$ alkaryl;
(k) $C_7$-$C_{12}$ alkylaryl;
(l) polyester groups having the formula (5)

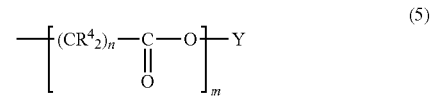

(5)

wherein R⁴ and Y are independently selected from the group consisting of hydrogen and $C_1$-$C_6$ linear or branched alkyl, n is 1-6 and m is 10 to 100;

(m) $C_1$-$C_{10}$ alkyl groups substituted with 1-4 ureido groups according to the formula (6)

(6)

wherein R⁵ is selected from the group consisting of hydrogen and $C_1$-$C_6$ linear or branched alkyl;

(n) polyether groups having the formula (7)

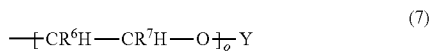
(7)

wherein Y, R⁶ and R⁷ are independently selected from the group consisting of hydrogen and $C_1$-$C_6$ linear or branched alkyl and o is 10-100; and wherein the 4H-unit is bonded to the polymer backbone P via R¹ and R² while R³ represents a side chain according to (a)-(h), or via R¹ and R³ while R² represents a side chain according to (a)-(h);

F represents a reactive end-group selected from the group consisting of hydroxy, amine, thiol, isocyanate, carboxylic acid, carboxylic ester, and combinations of these end groups;

v is in the range of 1-4;

w is in the range of 1-4;

L represents a linker moiety that is covalently linked to Z and is selected from (i) the group consisting of cyclic, linear or branched $C_1$-$C_{24}$ alkylene groups, $C_6$-$C_{24}$ arylene groups, $C_7$-$C_{24}$ alkarylene groups and $C_7$-$C_{24}$ arylalkylene groups and/or (ii) the group consisting of amino acid residues according to the formula (G):

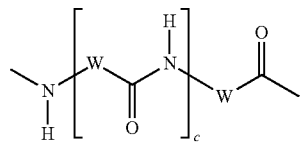
(G)

wherein W is a cyclic, linear or branched $C_1$-$C_{24}$ alkylene group;

c is 0-3; and

Z represents a group that can cross-link and is selected from a thiol group and an aryl group that contains 2 to 6 hydroxy groups.

10. A method of using the water gellant of claim 1 to prepare a hydrogel, a cosmetic or a biomedical product, the method comprising:

reacting
(a) 0.3-80.0 wt. %, based on the total weight of the formulation, of the water gellant; and
(b) 20.0 to 99.7 wt. % water;

with an auxiliary A that initiates or mediates the cross-linking reaction of the D moieties in the water gellant so as to prepare the hydrogel, cosmetic, or biomedical product.

11. A method of using the water gellant of claim 1 to form a liquid aqueous formulation, the method comprising:

admixing 0.3%-50.0% by weight of the water gellant with 50.0 to 99.7 wt. % of water so as to form the liquid aqueous formulation.

12. The method according to claim 11, further comprising admixing the liquid aqueous formulation with a biologically active or pharmaceutically active compound or a bioactive species.

13. A method of using the water gellant of claim 1 to form a hydrogel, the method comprising:

cross-linking groups D of the water gellant.

14. A method of using the water gellant of claim 1, the method comprising:

physically incorporating the water gellant into a biomedical or cosmetic product.

15. The method according to claim 14, further comprising:

utilizing the biomedical or cosmetic product for controlled drug-delivery, tissue engineering, wound-care, tissue-adhesion, tissue sealant, cardiac patch, transdermal patch, cardio-vascular structures, or as a coating for a medical device.

* * * * *